(12) United States Patent
Cross et al.

(10) Patent No.: US 9,504,791 B2
(45) Date of Patent: Nov. 29, 2016

(54) MEDICATED MODULE WITH USER SELECTION

(75) Inventors: John David Cross, Long Buckby (GB); Malcolm Stanley Boyd, Wellsbourne (GB); Alasdair George Young, Chippins Norton (GB); Naceur Rekaya, Leamington Spa (GB); James Alexander Davies, Leamington Spa (GB); Steven Wimpenny, Leamington Spa (GB); Daniel Thomas De Sausmarez Lintell, Rugby (GB); Simon Lewis Bilton, Leamington Spa (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 1093 days.

(21) Appl. No.: 13/582,013

(22) PCT Filed: Mar. 23, 2011

(86) PCT No.: PCT/EP2011/054422
§ 371 (c)(1),
(2), (4) Date: Oct. 31, 2012

(87) PCT Pub. No.: WO2011/117284
PCT Pub. Date: Sep. 29, 2011

(65) Prior Publication Data
US 2013/0041321 A1 Feb. 14, 2013

Related U.S. Application Data

(60) Provisional application No. 61/317,548, filed on Mar. 25, 2010, provisional application No. 61/331,914, filed on May 6, 2010.

(30) Foreign Application Priority Data

Jul. 21, 2010 (EP) .................................. 10170281
Jul. 21, 2010 (EP) .................................. 10170283

(51) Int. Cl.
*A61M 5/24* (2006.01)
*A61M 5/32* (2006.01)
(Continued)

(52) U.S. Cl.
CPC ........... *A61M 5/2448* (2013.01); *A61M 5/326* (2013.01); *A61M 5/2466* (2013.01);
(Continued)

(58) Field of Classification Search
CPC ............ A61M 5/2448; A61M 5/326; A61M 5/31533; A61M 5/3272; A61M 2005/3247; A61M 2005/1787; A61M 2005/3267; A61M 5/3294
See application file for complete search history.

(56) References Cited

U.S. PATENT DOCUMENTS 4,425,120 A * 1/1984 Sampson ............ A61M 5/3271
604/198
6,562,002 B1 5/2003 Taylor
(Continued)

FOREIGN PATENT DOCUMENTS

JP H01-500803 3/1989
JP 2005-510308 4/2005
(Continued)

OTHER PUBLICATIONS

Japanese Office Action for JP App. No. 2013-500487, mailed Jan. 6, 2015.
(Continued)

*Primary Examiner* — Bradley Osinski
(74) *Attorney, Agent, or Firm* — McDonnell Boehnen Hulbert & Berghoff LLP (57) ABSTRACT

A medicated module for an injection system to co-deliver at least two medicaments is disclosed where a primary delivery device containing a primary medicament accepts a medicated module containing a single dose of a secondary medicament and where both medicaments are delivered through a hollow needle. The medicated module is user selectable so that it will deliver a priming dose of a primary medicament or both the primary and secondary medicaments. The module also contains a needle guard that locks after dose delivery. The needle guard prevents accidental needle sticks before and after an injection. A locking collar rotates during use as an inner protrusion follows three paths of a track located on the outer surface of a body housing. When the inner facing protrusion is in the third path, it encounters a hard stop and a rotational bias that locks the guard from further refraction and thus covers the sharp distal end of the needle.

5 Claims, 5 Drawing Sheets (51) Int. Cl.
   *A61M 5/31*     (2006.01)
   *A61M 5/315*    (2006.01)
   *A61M 5/34*     (2006.01)
   *A61M 5/178*    (2006.01)

(52) U.S. Cl.
   CPC ....... *A61M 5/3146* (2013.01); *A61M 5/31525* (2013.01); *A61M 5/31533* (2013.01); *A61M 5/3272* (2013.01); *A61M 5/3294* (2013.01); *A61M 5/347* (2013.01); *A61M 2005/1787* (2013.01); *A61M 2005/3247* (2013.01); *A61M 2005/3267* (2013.01); *A61M 2205/583* (2013.01)

(56) References Cited

U.S. PATENT DOCUMENTS

| | | | | |
|---|---|---|---|---|
| 8,663,172 | B2* | 3/2014 | Davies | A61M 5/284 604/187 |
| 2001/0037087 | A1* | 11/2001 | Knauer | A61M 5/204 604/137 |
| 2002/0004648 | A1 | 1/2002 | Larsen et al. | |
| 2006/0276755 | A1 | 12/2006 | Sullivan et al. | |
| 2009/0018506 | A1 | 1/2009 | Daily et al. | |

FOREIGN PATENT DOCUMENTS

| | | |
|---|---|---|
| JP | 2009-506815 | 2/2009 |
| WO | 88/02265 | 4/1988 |
| WO | 01/76665 | 10/2001 |
| WO | 03/045480 | 6/2003 |
| WO | 2007/026163 | 3/2007 |

OTHER PUBLICATIONS

International Search Report and Written Opinion for Int. App. No. PCT/EP2011/054422, mailed Jun. 21, 2011.

International Preliminary Report on Patentability for Int. App. No. PCT/EP2011/054422, issued Sep. 25, 2012.

* cited by examiner

MEDICATED MODULE WITH USER SELECTION

CROSS REFERENCE TO RELATED APPLICATIONS

The present application is a U.S. National Phase Application pursuant to 35 U.S.C. §371 of International Application No. PCT/EP2011/054422 filed Mar. 23, 2011, which claims priority to U.S. Provisional Patent Application No. 61/317,548 filed Mar. 25, 2010 and U.S. Provisional Patent Application No. 61/331,914 filed May 6, 2010. The present application also claims priority to European Patent Application No. 10170281.9 filed Jul. 21, 2010 and European Patent Application No. 10170283.5 filed Jul. 21, 2010. The entire disclosure contents of these applications are herewith incorporated by reference into the present application.

FIELD OF THE INVENTION

Specific embodiments of this disclosure relate to medical devices and methods of delivering at least two drug agents from separate reservoirs using devices having only a single dose setting mechanism and a single dispense interface. A single delivery procedure initiated by the user may cause a non-user settable dose of a second drug agent or secondary medicament and a variable set dose of a first drug agent or primary medicament to be delivered to the patient. The drug agents may be available in two or more reservoirs, containers or packages, each containing independent (single drug compound) or pre-mixed (co-formulated multiple drug compounds) drug agents. Specifically, the present disclosure concerns a medicated module where the user has to select whether to dispense the second drug agent or to bypass the second drug agent and only dispense the first drug agent. The present disclosure is of particular benefit where the therapeutic response can be optimized for a specific target patient group, through control and definition of the therapeutic profile.

BACKGROUND

Certain disease states require treatment using one or more different medicaments. Some drug compounds need to be delivered in a specific relationship with each other in order to deliver the optimum therapeutic dose. The present disclosure is of particular benefit where combination therapy is desirable, but not possible in a single formulation for reasons such as, but not limited to, stability, compromised therapeutic performance and toxicology.

For example, in some cases it might be beneficial to treat a diabetic with a long-acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example, one or more actives may require a titration period to gradually introduce a patient up to a "maintenance" dose. A further example would be if one active requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems may arise where a multi-drug compound therapy is required, because many users cannot cope with having to use more that one drug delivery system or to make the necessary accurate calculation of the required dose combination. This is especially true for users with dexterity or computational difficulties. In some circumstances it may also be necessary to perform a priming procedure of the device and/or needle cannulae before dispensing the medicaments. Likewise, in some situations, it may be necessary to bypass one drug compound and to dispense only a single medicament from a separate reservoir.

Accordingly, there exists a strong need to provide devices and methods for the delivery of two or more medicaments in a single injection or delivery step that is simple for the user to perform. The present disclosure overcomes the above-mentioned problems by providing separate storage containers for two or more active drug agents that are then only combined and/or delivered to the patient during a single delivery procedure. Setting a dose of one medicament may automatically fix or determine the dose of the second (i.e. non-user settable) medicament. The present disclosure also gives the opportunity for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime.

The present disclosure also provides a medicated module that allows the user to select whether medicaments from two reservoirs are dispensed together or whether the secondary medicament in the module is bypassed, e.g. to provide delivery of only one medicament as a non-receivable (i.e. not able to inject) priming dose.

These and other advantages will become evident from the following more detailed description of the invention.

One problem to be solved by the present invention is to provide a medicated module and a drug delivery system where the safety for the user is improved.

SUMMARY

The present disclosure allows complex combinations of multiple drug compounds within a single drug delivery system. The disclosure allows the user to set and dispense a multi-drug compound through one single dose setting mechanism and a single dispense interface. This single dose setter controls the mechanism of the device such that a predefined combination of the individual drug compounds is delivered when a single dose of one of the medicaments is set and dispensed through the single dispense interface.

By defining the therapeutic relationship between the individual drug compounds, the disclosed drug delivery device would help to ensure that a patient/user receives the optimum therapeutic combination dose from a multi-drug compound device without the inherent risks associated with multiple inputs where the user has to calculate and set the correct dose combination every time he uses the device. The medicaments can be fluids, defined herein as liquids or powders that are capable of flowing and that change shape at a steady rate when acted upon by a force tending to change its shape. Alternatively, one of the medicaments may be a solid that is carried, solubilized or otherwise dispensed with another fluid medicament.

This disclosure is of particular benefit to users with dexterity or computational difficulties as the single input and associated predefined therapeutic profile removes the need for them to calculate their prescribed dose every time they use the device and the single input allows considerably easier setting and dispensing of the combined compounds.

In a preferred embodiment, a master or primary drug compound, such as insulin, contained within a multiple dose, user selectable device could be used with a single use, user replaceable, module that contains a single dose of a secondary medicament and the single dispense interface. When connected to the primary device, the secondary compound may be activated/delivered on dispense of the primary compound. Although the present disclosure specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with the drug delivery system and the medicated module of the present disclosure.

The term "insulin" shall mean Insulin, insulin analogs, insulin derivatives or mixtures thereof, including human insulin or a human insulin analogs or derivatives. Examples of insulin analogs are, without limitation, Gly(A21), Arg (B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

One aspect relates to a medicated module attachable to a drug delivery device. The medicated module may comprise a housing and at least one needle cannula. The needle cannula may be a double ended needle cannula. The medicated module may further comprise a reservoir. The reservoir may be arranged within the housing and may comprise a single dose of a medicament. The reservoir may already be arranged within the housing of the medicated module before the medicated module is attached to the device. The medicated module may comprise a needle guard. The needle guard may be adapted and arranged to provide protection of the at least one needle cannula. The medicated module may further comprise a selector. The selector may be operably connected to the reservoir. The selector may be configured to enable a user selection between different operating conditions of the module for enabling the reservoir to come into fluid engagement with the at least one needle cannula. The drug delivery device may be suitable to perform a dose setting and/or dose delivery operation for setting and/or delivering a dose of the first medicament when the device is not connected with the medicated module. The device onto which the medicated module is attachable is a separate unit which is able to operate also in absence of the medicated module.

According to an embodiment, the selector is operably connected to the needle guard. In particular, the selector may be, permanently or releasably, coupled to the needle guard such that the needle guard is prevented from rotation with respect to the selector. The needle guard may be, in a limited fashion, axially moveable with respect to the selector.

According to an embodiment, the reservoir is a single molded component having an internal cavity with an integral flow distributor. The flow distributor may be configured to guide flow of a fluid, e.g. a primary medicament held in the device to help expellinging the medicament, preferably substantially all of the medicament, in particular at least about 90% of the medicament, from the reservoir.

According to an embodiment the medicated module, in particular the reservoir may be pre-filled with a second medicament before the module is attached to the drug delivery device. In a further embodiment, the medicated module may be pre-filled with the second medicament before fluid communication is established between at least one of the needle cannulae and the reservoir of the primary device, i.e. the primary reservoir.

According to an embodiment the medicated module comprises a medicated needle. The medicated module comprises a proximal needle cannula. The medicated module comprises a distal needle cannula. The medicated module comprises the needle cannulae before the medicated module is attached to the device. The reservoir is arranged in an axial direction between the distal needle and the proximal needle. The medicated module is adapted and arranged for establishing fluid communication between the distal needle, the proximal needle and the reservoir.

According to an embodiment, the reservoir contains a liquid medicament. The medicament may comprise a GLP-1. Alternatively, the medicament may comprise a premix of insulin and a GLP-1.

The medicated module attachable to the drug delivery device is provided that comprises a housing having a proximal end, a distal end, and an outer surface, where the proximal end has a hub having a connector configured for attachment to the drug delivery device. There is the reservoir in the housing that contains a medicament. The medicated module assembly contains the needle guard that can reduce the risk of accidental needle sticks before and after use as well as reduce the anxiety of users suffering from needle phobia. The needle guard is preferably configured with a solid planar surface at its distal end that provides a large surface area that reduces the pressure exerted on the patient's skin, which may allows the user to experience an apparent reduction in the force exerted against the skin. Preferably, the planar surface covers the entire distal end of the needle guard with the exception of a small needle pass through hole aligned axially with the needle. This pass through hole is preferably no more than 10 times greater in diameter than the outer diameter of the needle cannula. For example, with a needle outside diameter of 0.34 mm, the pass through hole diameter D can be 3.4 mm. Preferably, the pass through hole size should be large enough for the user to see that the device is primed, i.e. that a drop or more of medicament is dispensed. This difference between the hole size and the cannula diameter is to allow for tolerances and also to allow users to see the drop of liquid on the end of the cannula after priming.

Further, the movable needle guard or shield may be configured to move axially in both the distal and proximal directions when pressed against an injection site. When the medicated module is removed or withdrawn from the patient, the needle guard may be returned to its original starting location and a rotating locking collar may securely lock into the housing through inwardly projecting protrusion or pip such that the guard will be locked from further substantial axial movement as described later on in more detail. By "substantial" movement we do not mean the typically amount of "play" in system, but instead we mean that the needle guard does not move axially a distance that exposes the distal end of the cannula.

According to an embodiment, the medicated module may be attachable to a drug delivery device, preferably a pen shaped injection device. The medicated module may comprise a housing having an outer surface, a proximal end, and a distal end. The proximal end of the housing may comprise a hub that has a connector configured for attachment to a drug delivery device. The hub can be a separate part from the housing or integral, for example molded as part of the housing. This connector can be any connector design, such as threads, snap fits, bayonet, lure lock, or combination of these designs.

Two needle cannulae may be used, a distal cannula and a proximal cannula. Both cannulae are preferably doubled-ended. The needle cannulae may be adapted and arranged for piercing a septum or seal and for piercing skin. The distal needle may be mounted in an end cap and the proximal needle may be mounted in a hub, each using any technique known to those skilled in the art, such as welding, gluing, friction fit, and the like. The medicated module may also contain two biasing members, preferably springs, one being a module spring and the other one being a needle guard spring. The module spring may comprise one end that engages the proximal face of an upper keeper of a capsule that contains the reservoir of the secondary medicament. The proximal end of the guard spring may engage the inner face of the housing and distal end may engage the needle guard. Although a preferred biasing member is a spring, any type of member that produces a biasing force will work.

According to an embodiment, the medicated module comprises a locking collar. The locking collar may comprise a bearing surface. The locking collar may comprise an inner surface. The inner surface may comprise at least one protrusion. The at least one protrusion may be configured to mechanically cooperate with at least one track provided on an outer surface of the housing. In particular each protrusion may be configured to mechanically cooperate with one respective track. The needle guard may be configured to engage the locking collar through the bearing surface.

According to an embodiment, the at least one track comprises a first, a second and a third path.

To prevent reuse of the needle assembly, the medicated module may includes the locking collar having an inner surface that surrounds a portion of the housing and that is free to move axially and helically within a defined track area on the outside surface of the housing. The inner surface of the collar can have the bearing surface, such as a crown and the inner facing protrusion or pip that may be slidably engaged with the track on the outer surface of the housing. Preferably, the crown comprises a number of distal facing angled surfaces (so-called "dog teeth") that act as bearing surfaces. These teeth may interact with similar angled faces on the needle guard that project proximally to cause the collar to experience a torque that is initially resisted by the interaction of the protrusion within the track when the needle guard is refracted during use. The proximally facing angled surfaces (i.e. another set of dog teeth) associated with the needle guard can be a separate part attached to the needle guard or can be integral to the needle guard. The angled surfaces may be configured to engage and bias the crown on the locking collar both rotationally and axially.

According to an embodiment, the selector comprises one or more tactile features. The tactile features may be adapted and arranged to be gripped by a user. The tactile features may be configured to allow movement of the selector with respect to the housing into one or more predetermined positions.

The medicated module may contain the selector that is operably connected to the needle guard in such a way that the user can move the selector, preferably by rotation, to allow the medicament in the reservoir, which in a preferred embodiment is contained in a self-contained capsule, to be dispensed along with the primary medicament, or to allow a primary medicament to bypass the reservoir to fulfill a priming function of the drug delivery device. Preferably, the selector comprises a raised gripping surface or protrusions projecting outwardly, or other like designed tactile features that may allow the user to easily and conveniently move the selector to one of two or more possible settings. The selector may have an indicator or window that shows the position of the selector. Preferably, the indicator is a pip, knob, button, or the like that protrudes through the outer surface of the rotating locking collar and visually shows the user the position of the selector. It may also be a visual indicator, e.g. showing colors or symbols, or a tactile or audible indicator. Preferably, user noticeable indicia indicate a pre-use priming position, a ready-to-use position, and a locked position of the needle guard after the medicated module has been used to perform an injection.

According to an embodiment, the selector may comprise at least two positions.

In a first position of the selector, the needle guard may be prevented from moving axially with respect to the housing. Furthermore, the needle cannula may not be in fluid communication with the reservoir. In a second position of the selector, movement of the needle guard in an axial direction with respect to the housing may be allowed. Furthermore, fluid communication of the needle cannula with the reservoir may be enabled.

According to an embodiment, when the needle guard is moved axially with respect to the housing when the selector is in the second position, the reservoir is moved in a proximal direction with respect to the housing to enable fluid engagement of the needle cannula with the reservoir.

Preferably, the selector can have the at least two positions. A first setting could be where the needle guard is locked from axial movement and the reservoir in the module is isolated such that the primary medicament contained in a separate reservoir can be used to prime the attached delivery device using, for example, a bypass around or through or independent of the reservoir in the module. The second position or setting of the selector could allow the needle guard to move axially during application/pressing the module to an injection site (whether or not the dose button is actually activated). Selection of this second position could cause the medicament in the module reservoir to come into fluid engagement with a dose dispense interface, such as a hollow needle cannula. A possible third position could also allow the needle guard to move axially, but not allow the medicament in the reservoir to be dispensed. In this possible third position, medicament from the primary reservoir located in the attached drug delivery device would bypass the module reservoir and would be dispensed directly through the single dispense interface.

According to an embodiment, the medicated module comprises an outer sleeve. The outer sleeve may be, permanently or releasably, fixed to the housing. The outer sleeve may be secured against axial and rotational movement with respect to the housing. The outer sleeve may be configured to mechanically cooperate with the selector, in particular with at least one track provided on the selector, such that movement of the selector with respect to the housing is enabled.

The selector may be operably connected to the module reservoir through indirect engagement with an end cap that abuts an inner housing at its distal end. The outer sleeve that covers the proximal end of the selector may have an inner surface with a radial pip or protrusion that travels in the track or path on the outer surface of a proximal portion of the selector. This track may be helical in shape and may be configured such that as the user rotates the selector, the selector, guard, end cap, inner housing, and reservoir all move in the proximal direction until the two needle cannulae come into fluid engagement with the reservoir, which is preferably a self-contained, sealed and sterile capsule containing a single dose of the secondary medicament. This secondary medicament can be the same or different from the first or primary medicament in contained in the drug delivery device that is configured to accept the medicated module.

Inside the housing there may be a cavity that contains the capsule that is positioned inside the inner housing. Preferably, when the selector is moved by the user to a predetermined position (for example to the second position) the inner housing and the reservoir may be moved proximally causing the cavity volume to decrease. This may allow the seals at the top and bottom of the capsule to be pierced by the needle cannulae such that the secondary medicament can be expelled from the reservoir during dose delivery. When connected to the drug delivery device containing the primary medicament and prior to piercing the seals of the reservoir, the needle cannulae are only in fluid communication with the first medicament. A fluid flow path may bypass the capsule. This fluid flow path or channel may be used in the priming function of the drug delivery device and possibly in the delivery of only the primary medicament. This bypass could be achieved by a number of means designed such that the primary medicament could flow to the dispense interface without interacting with the secondary medicament contained within the reservoir of the medicated module.

According to an embodiment, the needle guard is axially moveable with respect to the housing between an extended and a retracted position. The at least one protrusion may be configured to mechanically cooperate with the first and the second path of the respective track during retraction and partial extension of the needle guard. The at least one protrusion may be configured to mechanically cooperate with the third path of the respective track during final extension of the needle guard into a locking position. In the locking position, the needle guard may be fully extended. In the locking position, the needle guard may be configured to be prevented from further axial movement with respect to the housing.

According to an embodiment, the bearing surface comprises a crown. The crown may be provided on the inner surface of the locking collar. The crown may be configured to mechanically cooperate with a plurality of angled surfaces arranged on the proximal end of the needle guard to rotationally bias the collar.

According to an embodiment, the medicated module comprises a biasing member, e.g. a spring. The biasing member may be adapted and arranged to exert a, preferably axially directed, biasing force onto the needle guard and the locking collar.

According to an embodiment, the needle guard is, preferably permanently rotationally constrained by the selector. The locking collar may be, preferably permanently, rotationally constrained when the at least one protrusion mechanically cooperates with the first path of the respective track. The module may provide an audible and/or tactile indication to a user when the locking collar rotates under at least one of the following conditions: the at least one protrusion moves from the first path to the second path; a biasing torque may be created by mechanical interaction between the needle guard and the locking collar due to the biasing force exerted on the locking collar and the needle guard by the biasing member; a biasing torque may be created by the biasing member or an additional biasing member.

Preferably, there are one or more tracks located on the outside surface of the housing each having the set of first, second and third paths. On the inner surface of the locking collar there are one or more protrusions. The number of protrusions may correspond to the number of tracks. Each protrusion is configured to mechanically cooperate with, in particular to be guided by, one respective track. The protrusion travels in the first and second path of the respective track during retraction and partial extension of the needle guard. The protrusion moves to the third path and into the locking position when the needle guard is fully extended to its starting position. The needle guard is rotationally constrained by the selector preferably by the use of one or more spline features in the outer surface of the needle guard in cooperation with one or more followers or pips located at the distal end of the selector. The locking collar is rotationally constrained when the protrusion is in the first path of the track. As the protrusion is moved axially in the proximal direction when the needle guard pushes the locking collar during retraction, the protrusion moves from the first track to the second track causing the assembly to emit the audile sound and/or the tactile feedback. This may tell the user that the device has now been activated to lock upon extension of the needle guard in the distal direction.

According to an embodiment, the outer sleeve comprises at least one opening, e.g. a window. Preferably, the outer sleeve comprises three openings or windows such that the user may be able to view the opening or window irrespective of the position of the device with respect to the user. The opening may be configured for viewing indicia provided on an outer surface of the locking collar. The indicia may be configured to indicate a pre-use position, a ready-to-use position, where fluid engagement between the needle cannula and the reservoir may be established, and a locked position of the needle guard.

One aspect relates to a drug delivery system configured to deliver two or more medicaments operable through a single dispense interface. The drug delivery system may comprise a primary reservoir of medicament. The primary reservoir may contain at least one primary medicament. The drug delivery system may comprise a single dispense interface, e.g. a needle cannula. The dispense interface may be configured for fluid communication with the primary reservoir. The drug delivery system may comprise the previously described medicated module. The single dispense interface may be part of the medicated module.

According to an embodiment, the drug delivery system comprises a bypass. The bypass may be adapted and arranged for bypassing the reservoir of the medicated module. When the selector is in the first position, the primary medicament may be enabled to flow via the bypass and through the single dispense interface. When the selector is moved from the first position into the second position, the medicament in the reservoir of the medicated module may be allowed to be dispensed along with the primary medicament through the single dispense interface.

According to an embodiment, the medicated module comprises the bypass.

According to an embodiment, the drug delivery system comprises a dose button. The dose button may be operatively connected to the primary reservoir. Activation of the dose button may cause the primary medicament to be dispensed through the single dispense interface.

According to an embodiment, the drug delivery system comprises pen-type device, in particular a pen-type injector.

In one embodiment, there is the drug delivery system to deliver two or more medicaments operable through a single dose setter and a single dispense interface. The medicated module which is attachable to the drug delivery device may, as described above, comprise the housing having a proximal end and a distal end, where the proximal end has a hub with a connector configured for attachment to the drug delivery device and having a double-ended needle cannula for piercing the reservoir of primary medicament. The rotatable locking collar may surround the housing. The collar may have a bearing surface and an inner surface, where the inner surface may comprise the inwardly facing protrusion that is slidably engaged with the track on the outer surface of the housing. The reservoir may be positioned within the capsule inside the housing and may contain a single dose of the secondary medicament. The capsule preferably contains a flow distributor to ensure that substantially all the single dose of secondary medicament is forced out of the capsule by the primary medicament during an injection. The flow distributor can be a separate stand alone insert or pin. Alternatively, the flow distributor and the capsule together can be manufactured or assembled as a one-piece component where the flow distributor is integral with the capsule. Such a unitary construction can be achieved utilizing, for example, design principles such as form fit, force fit or material fit, such as welding, gluing, or the like, or any combination thereof. The one-piece component may comprise one or more medicament flow channels, preferably one flow channel. The capsule and/or flow distributor can be constructed of any material that is compatible to the primary and secondary medicaments. Preferably, the capsule and/or flow distributor can be made from compatible materials of construction that include, but are not limited to, COC (an amorphous polymer based on ethylene and norbonene, also referred to as cyclic olefin copolymer, ethylene copolymer, cyclic olefin polymer, or ethylene-norbornene copolymer), LCP (a liquid crystal polymer having an aramid chemical structure that includes linearly substituted aromatic rings linked by amide groups, and further can include partially crystalline aromatic polyesters based on p-hydroxybenzoic acid and related monomers and also highly aromatic polyesters), PBT (polybutylene terephthalate thermoplastic crystalline polymer or polyester), COP (a cyclic olefin polymer based on ring-opening polymerization of norbornene or norbornene-derivatives), HDPE (high density polyethylene), and SMMA (styrene methyl methacrylate copolymer based on methyl methacrylate and styrene). A preferred material is one that is typically used to manufacture septa or pistons (bungs) found in multi-dose medicament cartridges, however, any other material that is compatible with the drug could be used, e.g. glass, plastics or specific polymers, for example, TPE (thermo plastic elastomer), LSR (liquid silicone rubber), LDPE (low density polyethylene), and/or any kind of medical grade rubber, natural or synthetic. The movable guard may surround a portion of the housing to prevent needle sticks. The housing may comprise the distal end and the proximal end, where the proximal end may engage the locking collar through the bearing surface. Also included may be the selector operably connected to the reservoir and the outer sleeve fixed to the housing that may engage the track on the selector.

The present disclosure also covers a method of dispensing a fixed dose of a secondary medicament and a variable dose of a primary medicament from separate reservoirs. The method may involve the steps of first attaching a medicated module to a delivery device, the medicated module having a selector that can be placed in a starting or pre-use position and a second or ready-to-use position, where the pre-use position may be configured for priming only and the second position may be configured for a combination delivery of the two medicaments. With the selector in the starting or first position, the user can prime the drug delivery device using only the primary medicament and bypassing the secondary medicament. After priming, the user may select either the second or a possible third position of the selector. If the user has not already set a dose of the first/primary medicament, the user may then set a dose of the first medicament contained in the primary reservoir of the drug delivery device using a single dose setter. If the selector is set to the second position, then, when the user activates a dose button, the set dose of the first medicament from the primary reservoir may be caused to move in the distal direction and may simultaneously force substantially all of the non-user set dose (e.g. a single dose) of the secondary medicament from the secondary reservoir contained in the medicated module through the single dispense interface, preferably a hollow injection needle. Upon completion of the delivery procedure, substantially the complete amount of the secondary medicament has been expelled as well as the selected dose of the first medicament through the single dispense interface. By "substantially the complete amount" we mean that at least about 80% of the secondary medicament is expelled from the drug delivery device, preferably at least about 90% is expelled. Alternatively, if the selector is configured to have a third position, then if the selector is in the third position, the first medicament may be forced into a bypass channel around the second reservoir in the medicated module and only the first medicament may be dispensed. In either situation, it is preferred that the needle guard will prevent a second delivery or insertion through a locking mechanism as described previously.

The combination of compounds as discrete units or as a mixed unit is delivered to the body via an integral needle. This would provide a combination drug injection system that, from a user's perspective, would be achieved in a manner that very closely matches the currently available injection devices that use standard needles.

The medicated module can be designed for use with any drug delivery device with an appropriate compatible interface. However, it may be preferable to design the module in such a way as to limit its use to one exclusive primary drug delivery device (or family of devices) through employment of dedicated or coded features to prevent attachment of a non-appropriate medicated module to a non-matching device. In some situations, it may be beneficial to ensure that the medicated module is exclusive to one drug delivery device while also permitting the attachment of a standard drug dispense interface to the device. This would allow the user to deliver a combined therapy when the module is attached, but would also allow delivery of the primary compound independently through the standard drug dispense interface in situations, such as, but not limited to, dose splitting or top-up of the primary compound.

A particular benefit of the present disclosure may be that the medicated module makes it possible to tailor dose regimes when required, especially where a titration period is necessary for a particular drug. The medicated module could be supplied in a number of titration levels with obvious differentiation features such as, but not limited to, aesthetic design of features or graphics, numbering etc, so that a patient could be instructed to use the supplied medicated module in a specific order to facilitate titration. Alternatively, the prescribing physician may provide the patient with a number of "level one" titration medicated modules and then, when these are finished, the physician could prescribe the next level. A key advantage of this titration program may be that the primary device remains constant throughout.

According to a preferred embodiment, a medicated module is provided which is attachable to a drug delivery device. The medicated module comprises a housing comprising at least one needle cannula, and a reservoir arranged within the housing, the reservoir comprising a single dose of a medicament. The medicated module comprises a needle guard adapted and arranged to provide protection of the at least one needle cannula. The medicated module comprises a selector operably connected to the reservoir, the selector being configured to enable selection between different operating conditions of the module for enabling the reservoir to come into fluid engagement with the at least one needle cannula.

According to a preferred embodiment, a medicated module is provided which is attachable to a drug delivery device. The medicated module comprises a housing having a proximal end and a distal end, where the proximal end has a hub comprising a connector configured for attachment to a drug delivery device and a double-ended needle cannula. The medicated module comprises a locking collar having a bearing surface and an inner surface, where the inner surface has an inwardly facing protrusion that is slidably engaged with a track on the outer surface of the housing. The medicated module comprises a reservoir within the housing comprising a single dose of a medicament. The medicated module comprises a guard having a distal end and a proximal end, where the proximal end engages the locking collar through the bearing surface. The medicated module comprises a selector operably connected to the reservoir. The medicated module comprises an outer sleeve fixed to the housing that engages a track on the selector.

According to a preferred embodiment, a drug delivery system is provided comprising a primary reservoir of medicament containing at least one primary medicament, a single dispense interface configured for fluid communication with the primary reservoir, and the previously described medicated module.

According to a preferred embodiment, a drug delivery system to deliver two or more medicaments is provided which, the drug delivery system being operable through a single dispense interface. The drug delivery system comprises a primary reservoir of medicament containing at least one drug agent, a dose button operably connected to the primary reservoir of medicament and a single dispense interface configured for fluid communication with the primary reservoir. Furthermore, the drug delivery system comprises a medicated module comprising a housing having a proximal end and a distal end, where the proximal end has a hub comprising a connector configured for attachment to a drug delivery device and a double-ended needle cannula. The medicated module furthermore comprises a locking collar having a bearing surface and an inner surface, where the inner surface has an inwardly facing protrusion that is slidably engaged with a track on the outer surface of the housing. The medicated module furthermore a reservoir within the housing comprising a single dose of a medicament, a guard having a distal end and a proximal end, where the proximal end engages the locking collar through the bearing surface, a selector operably connected to the reservoir, and an outer sleeve fixed to the housing that engages a track on the selector.

In a preferred embodiment, the primary drug delivery device is used more than once and therefore is multi-use, however, the drug delivery device may also be a single use disposable device. Such a device may or may not have a replaceable reservoir of the primary drug compound, but the present disclosure is equally applicable to both scenarios. It is also possible to have a suite of different medicated modules for various conditions that could be prescribed as one-off extra medication to patients already using a standard drug delivery device. Should the patient attempt to reuse a previously used medicated module, the present disclosure includes the locking needle guard that is activated after drug dispense or insertion that could alert the patient to this situation. Visual warnings (e.g. change in color and/or warning text/indicia within an indication window on the module once insertion and/or fluid flow has occurred) can also be used. Additionally, tactile feedback (presence or absence of tactile features on the outer surface of the module hub following use) could be used as well.

A further feature of this embodiment is that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant or who have computational or dexterity difficulties.

The present disclosure also covers a method of delivering two medicaments stored in separate primary packages. The medicaments may be both liquid, or alternatively, one or more of the medicaments may be a powder, suspension or slurry. In one embodiment, the medicated module could be filled with a powdered medicament that is either dissolved or entrained in the primary medicament as it is injected through the medicated module.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which.

DETAILED DESCRIPTION

Figure 1:
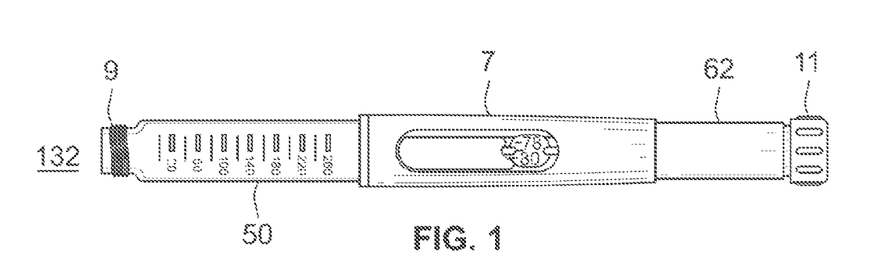
FIG. 1 illustrates one possible drug delivery device that can be used with the medicated module of the present disclosure.

In the present disclosure, a fixed predetermined dose of a secondary drug compound (secondary medicament) and a variable dose of a primary or first drug compound (primary medicament) may be administered through a single output or drug dispense interface. Setting the dose of the primary medicament by the user may automatically determine the fixed dose of the secondary medicament, which preferably is a single dose contained in a capsule or reservoir having an integral flow distributor. In a preferred embodiment, the drug dispense interface is a needle cannula (hollow needle). FIG. 1 illustrates one example of a drug delivery device 7 that the medicated module 4 (see FIGS. 2-4) can be attached to. The medicated module 4 may be attached to a connection means 9 on cartridge holder 50 of a distal end 132 of the device 7. Each medicated module 4 is preferably self-contained and provided as a sealed and sterile disposable module that has an attachment means 8 (see FIG. 4) compatible to the attachment means 9 at the distal end 132 of device 7. Although not shown, the medicated module 4 could be supplied by a manufacturer in a protective and sterile container, where the user would peel or rip open a seal or the container itself to gain access to the sterile medicated module 4. In some instances it might be desirable to provide two or more seals for each end of the medicated module 4.

Figure 2:
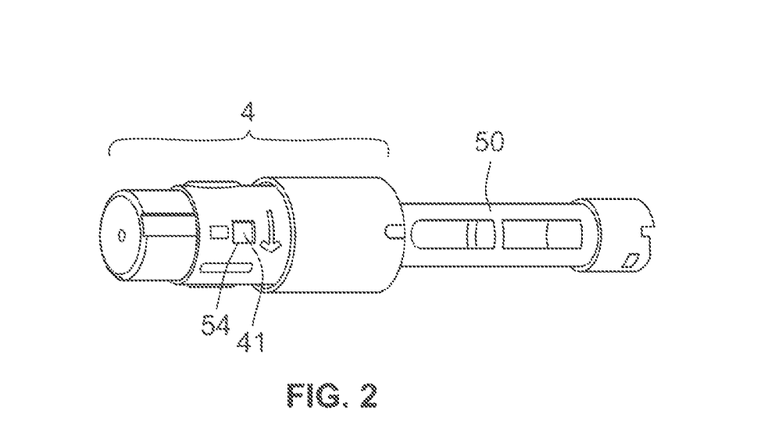
FIG. 2 illustrates an embodiment of the medicated module having a user settable selector feature, where the medicated module is attached to a cartridge holder of the drug delivery device of FIG. 1.
Figure 3:
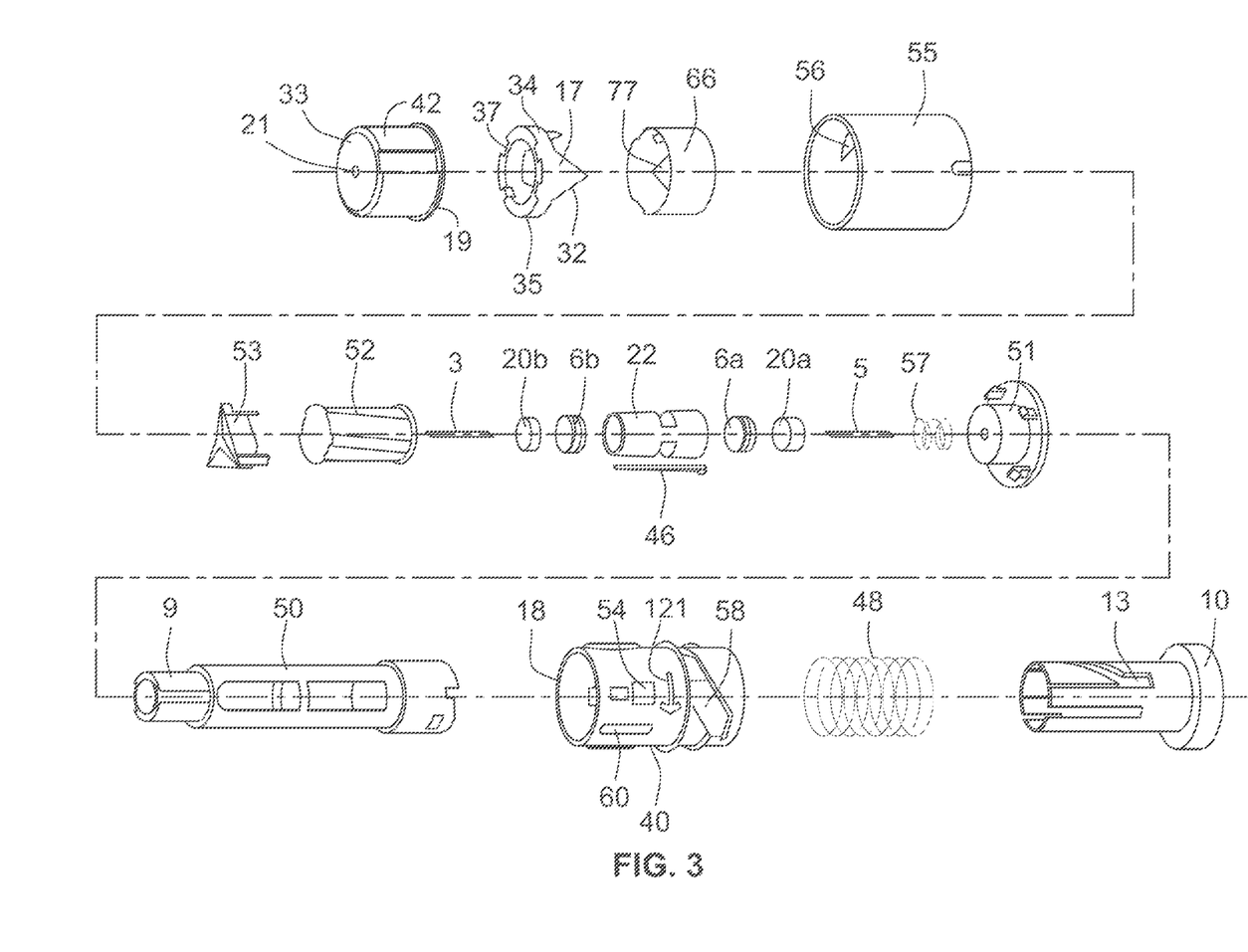
FIG. 3 illustrates an exploded perspective view of all the components of the medicated module illustrated in FIG. 2.
Figure 4:
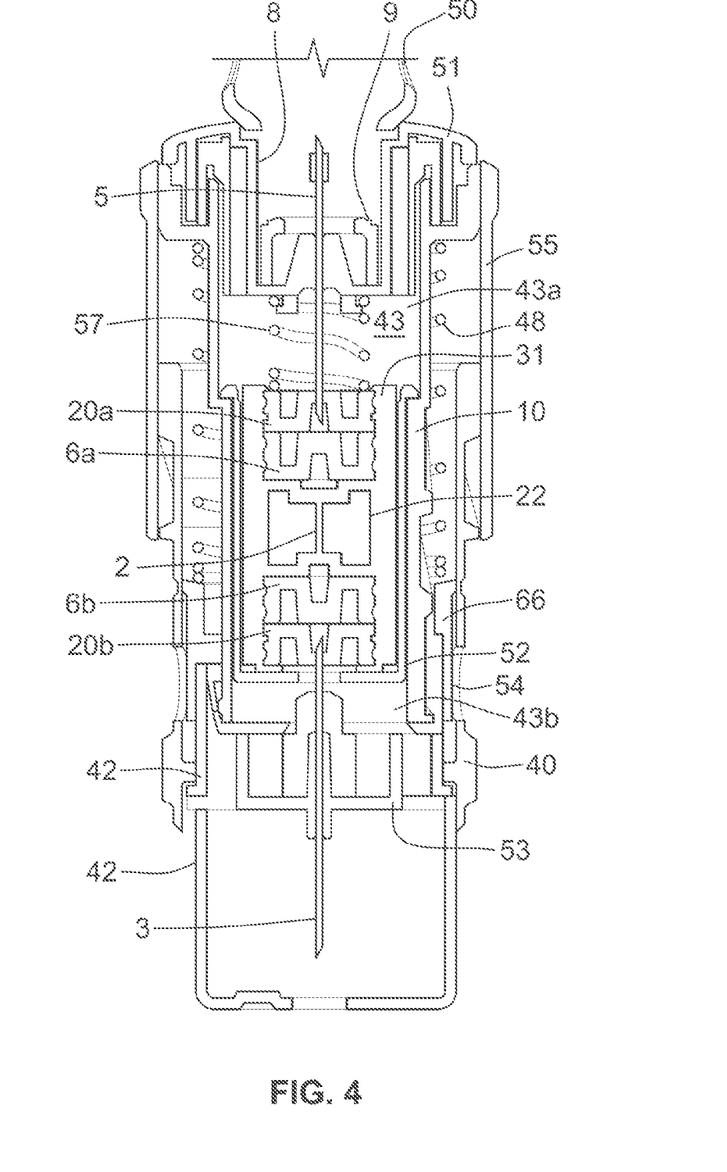
FIG. 4 is a sectioned view of the embodiment of the medicated module shown in FIG. 2 orientated in the bypass configuration.

Any known attachment means 8 can be used to attach the medicated module 4 to the chosen drug delivery device 7, including all types of permanent and removable connection means, such as threads, snap locks, snap fits, luer locks, bayonet, snap rings, keyed slots, and combinations of such connections. FIGS. 2-4 illustrate the attachment means 9 as a unique male luer lock type connection that is keyed specifically to a corresponding female luer lock type connection 8 on a hub 51 (see FIG. 3) of the medicated module 4. The embodiments shown in FIGS. 2-4 have the benefit of the secondary medicament 2 as a single dose being contained entirely within a capsule 31, and specifically in a reservoir 22, hence minimizing the risk of material incompatibility between the secondary medicament 2 and the materials used in the construction of the medicated module 4, specifically housing 10, inner housing 52, or any of the other parts used in the construction of the medicated module 4.

To minimize the residual volume of the secondary medicament 2, caused by recirculation and/or stagnant zones, that might remain in capsule 31 at the end of the dispense operation, it is preferable to have a flow distributor 23 (see FIG. 10) as an integral part of reservoir 22. The reservoir 22 containing the single dose of the secondary medicament 2 can be sealed with septa 6a and 6b (see FIG. 3), which are fixed to the capsule 31 using keepers or plugs 20a and 20b. Preferably, the keepers 20a, 20b have fluid channels that are in fluid communication with needles 3 and 5 and with a bypass 46 (see FIG. 3). Together this fluid path allows priming of the device 7 before injection. Preferably, the reservoir 22, flow distributor 23, keepers 20a, 20b, and bypass 46 can be made from materials that are compatible with the primary medicament. Examples of compatible materials of construction include, but are not limited to, COC (an amorphous polymer based on ethylene and norbonene, also referred to as cyclic olefin copolymer, ethylene copolymer, cyclic olefin polymer, or ethylene-norbornene copolymer); LCP (a liquid crystal polymer having an aramid chemical structure that includes linearly substituted aromatic rings linked by amide groups, and further can include partially crystalline aromatic polyesters based on p-hydroxybenzoic acid and related monomers and also highly aromatic polyesters); PBT (polybutylene terephthalate thermoplastic crystalline polymer or polyester); COP (a cyclic olefin polymer based on ring-opening polymerization of norbornene or norbornene-derivatives); HDPE (high density polyethylene); and SMMA (styrene methyl methacrylate copolymer based on methyl methacrylate and styrene). The needle pierceable septa, bungs, and/or seals that are used with both the capsule and the primary medicament cartridge can be manufactured using TPE (thermo plastic elastomer); LSR (liquid silicone rubber); LDPE (low density polyethylene); and/or any kind of medical grade rubber, natural or synthetic.

The design of flow distributor 23 should ensure that at least about 80% of the secondary medicament 2 is expelled from reservoir 22 through the distal end of needle 3. Most preferably, at least about 90% should be expelled. Ideally displacement of the first or primary medicament from the primary reservoir or cartridge in cartridge holder 50 through the capsule 31 will displace the secondary medicament 2 without substantial mixing of the two medicaments.

Attachment of the medicated module 4 to the multi-use device 7 causes proximal needle 5 to penetrate a septum (not shown) sealing the distal end of cartridge in cartridge holder 50 of the multi-use device 7. Once needle 5 has passed through the septum of the cartridge, fluid connection is made between the primary medicament and the needle 5. At this point, with a selector 40 (see FIG. 3) of the medicated module 4 in the starting position, the system can be primed by dialing out a small number of units (or cocking the device 7 if only a single dose selection is possible) using a dose dial sleeve or dose setter 62. If the selector 40 is set to the second position, dispense of the medicaments is then achieved via activation of a dose button 11 on device 7. The dose button 11 can be any triggering mechanism that causes the dose of the first medicament that was set by the dose setter 62 to move towards the distal end 132 of the device 7. In a preferred embodiment, the dose button 11 is operably connected to a spindle (not explicitly shown) that engages a piston in the primary reservoir of the first medicament. In a further embodiment, the spindle is a rotatable piston rod comprising two distinct threads.

One embodiment of the medicated module 4 is illustrated in FIGS. 2-4. In these embodiments, the medicated module 4 contains the capsule 31 comprising the reservoir 22, two keepers 20a and 20b, and two septa 6a and 6b. Reservoir 22 contains a fixed single dose of the secondary medicament 2. In some cases this secondary medicament 2 may be a mixture of two or more drug agents that can be the same or different from the primary drug compound in the drug delivery device 7. Preferably, the capsule 31 is permanently fixed within the medicated module 4, however, in some cases it may be preferred to design the module 4 such that the capsule 31 can be removed when empty and replaced with a new capsule.

In the embodiments shown in FIGS. 3-4, capsule 31 has ends that are sealed with the pierceable membranes or septa 6a and 6b that provide a hermetically sealed and sterile reservoir 22 for the secondary medicament 2. The primary or engagement needle 5 can be fixed in hub 51 connected to the proximal end of housing 10 of the module 4 and configured to engage capsule 31 when selector 40 is moved to a predetermined position as described below. The output or distal needle 3 is preferably mounted in an end cap 53 and initially protrudes into lower seal 20b. The proximal end of needle 3 pierces the lower septum 6b when the volume of a cavity 43 (see FIG. 4) within housing 10 is decreased as the selector 40 is moved to a predetermined setting.

During use, attachment of the medicated module 4 to a multi-use device, such as the one shown in FIG. 1, causes the proximal end of primary needle 5 to pierce the septum at the distal end of a cartridge contained in cartridge holder 50 of device 7. When first attached to the delivery device 7, the medicated module selector 40 is set at a pre-use or starting position. Preferably, an indicator 41 shows through a window 54 to inform the user of the pre-use condition of the medicated module 4. The selector 40 preferably is a tubular component positioned partially inside an outer sleeve 55 and engaged with a pip 56 on the inner surface of the sleeve 55. Gripping surfaces or other tactile features 60 assist a user in rotating the selector 40. Housing 10 partially defines the internal cavity 43 that holds inner housing 52, which contains capsule 31. Needle 3 is mounted to the end cap 53. A portion of the proximal end of housing 10 defines a top portion cavity 43a and a distal portion of the housing 10 defines a lower portion 43b of the cavity 43 (see FIG. 4).

FIG. 4 shows a cutaway view of the medicated module 4 attached to the cartridge holder 50 of the delivery device 7 where the selector 40 is positioned in the pre-use or starting position. In this position, the cavity 43 is at its largest volume and needles 3 and 5 are not in fluid communication with the secondary medicament 2 contained in the capsule 31. The capsule 31 is supported by inner housing 52 and is biased in distal direction by a spring 57, which prevents the capsule 31 from penetration by needle 5 until required. Additionally, the spring 57 may provide a biasing force, in combination with the frictional wall forces between the proximal keeper 20a and septum 6a and the walls of the capsule 31, to offset any axial displacement of the septum 6a or keeper 20a that may occur because of hydraulic pressure generated in the flow cavity during fluid delivery, especially at high dispense speeds. In this neutral or suspended state of capsule 31, the primary medicament from the cartridge in cartridge holder 50 can flow through needle 5 into a void space between keeper 20a and septum 6a, through a side hole 38 in capsule 22 (see FIG. 10) into bypass 46, back into another side hole (not shown) and into a void space between septum 6b and keeper 20b, and eventually out through needle 3. This flow configuration allows the user to perform a priming step or procedure by setting a small dose of the primary medicament using the dose setter 62 and dose button 11 on the drug delivery device 7.

Figure 6:
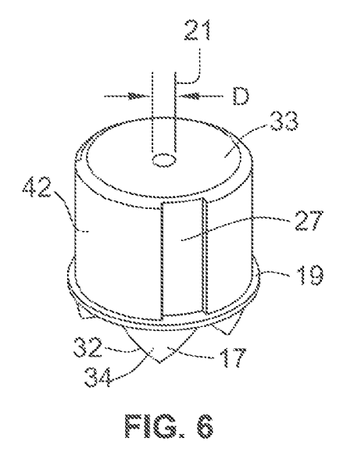
FIG. 6 illustrates a perspective view of the needle guard of the medicated module of FIG. 2.
Figure 7:
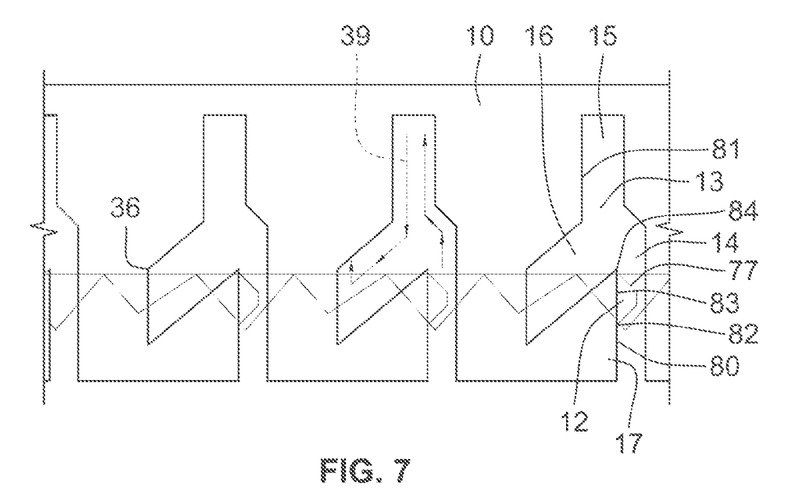
FIG. 7 illustrates the path of the track and the starting position of the protrusion of the medicated module of FIG. 2.

A compression spring 48 acts between the housing 10 and a locking collar 66 to bias a needle guard 42 into an extended (guarded) or distal position as illustrated in FIG. 4. The locking collar 66 has an inside surface 26 that has a crown 77 (see FIG. 5), which comprises one or more inwardly protruding features, protrusions, pips, or like structures 12, wherein each protrusion 12 runs in one respective track 13 or guide way formed in the outer surface of housing 10. As shown in FIG. 7, the respective track 13 has three paths, 14, 15, and 16, that have a specific geometry such that after a single use of the medicated module 4 the inwardly protruding features 12 are blocked from further axial movement and the needle guard 42 (and, hence, the device 7) is "locked" in a guarded position where the distal end of the needle 3 is completely and safety covered by the needle guard 42. Crown 77 comprises one or more angled distal facing bearing surfaces to engage like surfaces 17 facing proximally on a key 34 that is on or connected to the needle guard 42 (see FIG. 6).

The needle guard 42 is rotationally constrained by the selector 40 through one or more splined engagements 27, e.g. notches (FIG. 3). Although spring 48 biases needle guard 42 in the distal direction, the needle guard 42 is retained in selector 40 by interaction between a retention ridge 18 on the distal end of selector 40 and proximal lip 19 of the needle guard 42. Additionally, in the pre-use position, the needle guard 42 is locked from axial movement by a locking feature comprising stops (not shown) located on the inner side of the selector 40 and a lip 35 on key 34. When the user rotates selector 40 to the use position, the needle guard 42 rotates with it and relative to stationary key 34.

This rotation aligns cut out 37 portions on lip 35 of key 34 (see FIG. 3) and the stops on the inside of the selector 40, thereby allowing axial movement of the needle guard 42 (and of the key 34) relative to the selector 40. The crown 17 at the proximal end of the needle guard 42 located on key 34 interacts through proximally facing bearing surfaces 32 or "dog teeth" with the similar crown 77 formed on the inner side of the locking collar 66.

One unique feature of our medicated module assembly is the user feedback that is given when the assembly is used. In particular, the assembly emits an audible and/or tactile "click" to indicate to the user that the needle guard 42 will lock safely out upon completion of the injection. This audible and/or tactile feature works as follows. As mentioned, the needle guard 42 is rotationally constrained by the selector 40. The set of dog teeth 32 on the crown 17 at the proximal end of the key 34 interact with a similar set of dog teeth 131 formed on the inside of the locking collar 66 (see FIGS. 5 and 6). In the initial position, the two sets of teeth 32, 131 are unable to completely mesh, i.e., they are in an axially biased engagement as best shown by FIG. 7. Likewise, needle guard 42 is rotationally constrained by the selector 40 and the locking collar 66 is rotationally constrained by its inwardly facing protrusion 12 interacting with path 14 of track 13. The spring 48 applies a force in the distal direction on the proximal end of the locking collar 66 such that the collar 66 is urged to move axially and is rotationally biased along the angled bearing surfaces 131 and 32. Due to the angled surfaces of dog teeth 131, 32, the axially directed force may tend to induce a rotation of the locking collar 66. However, this rotation may be prevented due to mechanical cooperation of the protrusion 12 and path 14 of track 13. In particular, the dog teeth 131 and 32 are prevented from meshing because a face 83 of protrusion 12 is biased against a wall 80 of track 13 (see FIG. 7). As the needle guard 42 pushes the locking collar 66 in the proximal direction, protrusion 12 will move proximal along path 14 of track 13 until a lower most edge 82 moves past point 84 on path 14. Once edge 82 clears point 84 following along path 39, the locking collar 66, along with protrusion 12, is free to rotate as the dog teeth 32, 131 try to mesh. This causes face 83 of protrusion 12 to collide with a wall 81 of path 15, which provides an audible sound, as well as a tactile feel, to the user indicating that the device is now ready for injection.

The rotational torque generated by the interaction of the dog teeth 31 and 131, in particular the angled surfaces of the dog teeth 32, 131, converts axial movement of the needle guard 42 into rotation of the locking collar 66 such that protrusion 12 is brought into mechanical cooperation with path 15. Accordingly, no rotational bias of the locking collar 66 is required, e.g. by means of spring 48. Alternatively, the rotational torque needed to cause the rotation of the locking collar 66 may be provided by spring 48 providing the previously mentioned axial bias and, additionally, a rotational bias. Alternatively, the rotational torque needed to cause the rotation of the locking collar 66 may be provided by an additional spring (not explicitly shown) or clamping arms (not explicitly shown). Alternatively, the locking collar 66 and the needle guard 42 do not have a crown of dog teeth 31, 132 such that the locking collar 66 is passively rotated by means of mechanical cooperation of the protrusion 11 and the track 13.

For the sake of simplicity and clarity the principle of the interaction between needle guard 42 and locking collar 66 has been explained referring to one single protrusion 12 and one track 13. Alternatively, a plurality of protrusions 12 and a corresponding number of tracks 13 may be provided for enabling mechanical cooperation between the needle guard 42 and the locking collar 66.

When selector 40 has been set to the second or ready-to-use position, the needle guard 42 can then be pushed in the proximal direction as a planar surface 33 of the needle guard 42 comes into contact with an injection site or other stationary surface. This proximal movement of the needle guard 42 pushes locking collar 66 also in the proximal direction. After a predetermined distance, which is set by the intersection of paths 14 and 15, the locking collar 66 is forced to rotate under the rotational torque generated by the interaction of the dog teeth 131 and 32 due to the biasing force exerted on the collar by spring 48. As described above, the collar 66 "snaps" around (i.e., slightly rotates) as the two sets of dog teeth 32, 131 seek to become meshed. This sudden rotational movement of the collar 66 and the abrupt collision of face 83 of the inwardly facing protrusion 12 with the side wall 81 of the path 15 provides the user with an audible and/or tactile "click," indicating that the point of no return has been reached, i.e., when the spring 48 returns the needle guard 42 to an extended position the device 7 will be locked irrespective of whether an injection has been performed after the "click" or not.

As mentioned, the distal end of the guard 42 has the planar surface 33 that provides an added measure of safety and reduces the pressure exerted by the needle guard 42 on the injection site during an injection with our needle assembly. Because the planar surface 33 substantially covers access to needle 3 the user is prevented from gaining access to the distal tip of the needle 3 after the assembly, in particular the needle guard 42, is in the locked position. Preferably, the diameter D of a needle pass through hole 21 (see FIG. 3) in the planar surface is no more than 10 times that of the outer diameter of needle cannula 3.

Figure 5:
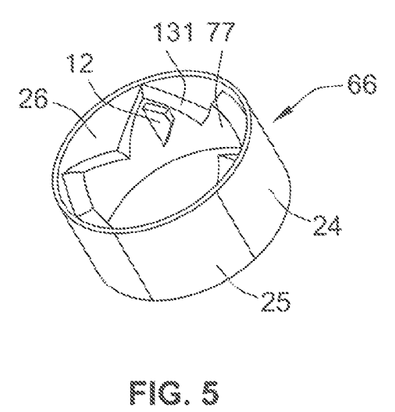
FIG. 5 illustrates a perspective view of the locking collar of the medicated module of FIG. 2.

The locking collar 66 preferably has indicia 41 that comprise preferably three different color vertical bands (bands 24 and 25 are shown in FIG. 5), each of which is sequentially visible through the opening or window 54 in the selector 40. The respective color designates the pre-use, ready-to-use, and locked states and, thus, provides the user with a visual notice of the condition of the medicated module 4. For example, a yellow color could be the pre-use position, a green color could indicate the module 4 is ready for injection. A band of red color could be used to indicate that the assembly has been used and is locked. Alternatively, graphics, symbols or text could be used in place of color or in combination with colors to provide this visual information/feedback.

Figure 8:
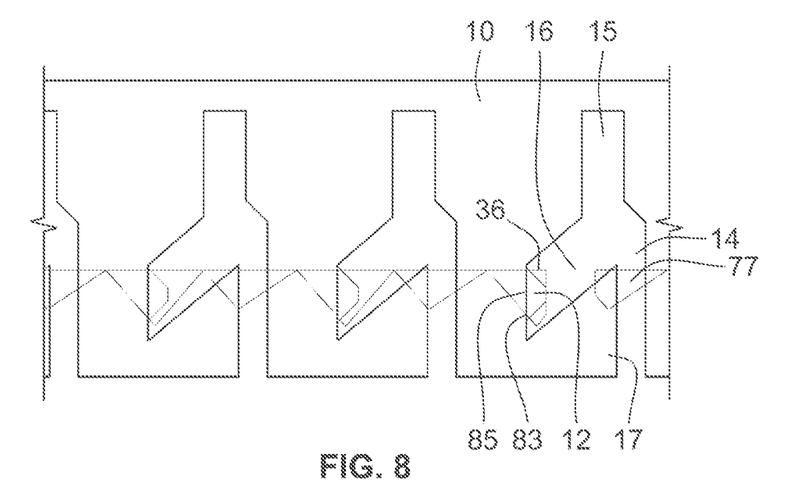
FIG. 8 illustrates the path of the track and the ending position of the protrusion of the medicated module of FIG. 2.

FIGS. 7 and 8 illustrate two-dimensionally the interaction of the dog teeth 32, 131 on both the needle guard 42 and collar 66 during injection. The figures illustrate the movement (see directional arrow 39) of the inwardly facing protrusion 12 from the initial position (FIG. 7) to the final locked position (FIG. 8) as the protrusions 12 on the locking collar 66 follow the paths 14, 15, 16 in track 13 on the outer surface of housing 10 as the locking collar 66 rotates and forces the protrusions 12, which move only axially, along the track 13. It is within the scope of the present disclosure that a number of tooth arrangements and/or profiles could be used to fulfill the required function described above, e.g., simple equal tooth profiles or more complex multi-angled profiles. The particular profile being dependent upon the required point of commit and rotation of the locking collar 66. FIGS. 7 & 8 illustrates a hard stop feature 36 in path 16 that prevents protrusion 12 from moving proximally after an injection. This hard stopping of the locking collar 66 likewise prevents guard 42 from substantial movement proximally, as defined earlier, from its initial start position and, thus, positions the needle guard 42 in a "locked out" safe position completely covering the distal end of needle 3. Additionally, face 83 of protrusion 12 is biased against a wall 85 of path 16, which further prevents refraction of the needle guard 42 because the collar 66 is prohibited from rotating. Applying a load to the needle guard 42 in the proximal direction encourages the 66 collar to rotate in a direction that reinforces the lock-out feature.

As mentioned above, when the selector 40 is in the pre-use or starting position, the needle guard 42 is locked and, thus, the needle 3 is inaccessible to an injection site and the user is unable to deliver a dose of the primary medicament alone or a combination of the primary and secondary medicaments. If the selector 40 is moved to a second or ready-to-use position, the needle guard 42 becomes unlocked and is free to travel in the proximal direction, thus exposing the needle 3 and allowing the user to administer a dose of the primary medicament and the single fixed dose of medicament 2 in capsule 31. This is because moving the selector 40 from the first position to the second position changes the volume in cavity 43 causing the capsule 31 to become fluidly engaged with needles 3 and 5. In the first or pre-use position, the user can prime the system with the primary medicament, but cannot inject a dose because the needle guard 42 is locked. Priming is possible because keepers 20*a* and 20*b*, septa 6*a* and 6*b*, along with bypass 46, form a fluid path or channel around capsule 31 so that the primary medicament can flow around or bypass the capsule 31 and exit direct through needle 3. Another benefit of the present disclosure is that, because the needle guard 42 is locked in the starting position and only priming of the device 7 is allowed, this prevents inadvertent use of the system, e.g. a user forgetting to rotate the selector 40 to engage the capsule 31 of secondary medicament and just attempting to deliver the primary medicament. A user who attempts to inject a dose in this way would not be able to get needle 3 into the skin and, thus, would not receive the set dose of either the primary or secondary medicament. At best, the user would experience a wet spot on his skin from dispensing (not injecting) the primary medicament through the bypass channel 46.

When the user rotates selector 40 in the direction specified by arrow 121, the pip 56 on the inner surface of the stationary outer sleeve 55 and engaged with a track 58 on the outer surface of selector 40 causes the selector 40 to move helically in the proximal direction. As pip 56 travels in track 58 during movement of the selector 40 to the ready-to-use or second position, it will eventually engage a stop at the end the track 58 that prevents further movement of the selector 40 because pip 56 drops into a void at the end of track 58, the lower surface of which is raised up slightly at the end nearest the void, to form essentially a clip feature. Thus, the trailing edges of both parts form an abutment wall once they have been rotated to this position. Only excessive force would cause the non-return features in track 58 to be overcome. Having this so-called "soft" stop or detent feature would allow a user to correct himself if he forgets to prime before establishing fluid engagement with the reservoir 22. However, in certain circumstances it may be necessary to prevent the user from reversing the rotation of the selector 40. As such, it may be beneficial to include in the track locking features that completely prevents the user from de-selecting the second position. This lockout feature can be accomplished in a variety of ways, including non-reversible detents or snap-locks.

Because the needle guard 42 is rotationally constrained relative to the selector 40, the needle guard 42 likewise moves proximally when the selector 40 is rotated, thus pushing end cap 53, inner housing 52 and capsule 31 to compress module spring 57. This allows cannulae 3 and 5 to pierce seals 6*a* and 6*b* and become fluidly connected with the secondary medicament 2 in capsule 31. This proximal movement reduces the volume of cavity 43. The start position of the selector 40 with the initial engagement of the capsule 31 with needles 3 and 5 is shown in FIG. 4. With the selector 40 set to the second position or ready-to-use position, the needle guard 42 is unlocked and is able to move proximally to expose the needle 3 for dose delivery. However, because needles 3 and 5 are in fluid engagement with the secondary medicament 2, the system cannot be primed without accidentally losing or wasting secondary medicament 2. Additionally, because the 3, 5 needles are pushed into the septa 6*a*, 6*b* and out of fluid communication with the keepers 20*a*, 20*b*, the bypass channel 46 used for priming is lost or no longer useable.

In any of the above described embodiments the secondary medicament 2 may be either in a powdered solid state, any fluid state contained within the secondary reservoir 22 or microcapsule, or coated to the inside surface of the drug dispense interface. The greater concentration of the solid form of the secondary medicament 2 has the benefit of occupying a smaller volume than the liquid having lower concentration. This, in turn, reduces the ullage of the medicated module 4. An additional benefit is that the solid form of the secondary medicament 2 is potentially more straightforward to seal in the reservoir 22 than a liquid form of the secondary medicament 2. The device 7 would be used in the same manner as the preferred embodiment with the secondary medicament 2 being dissolved by the primary medicament during dispense.

Figure 9:
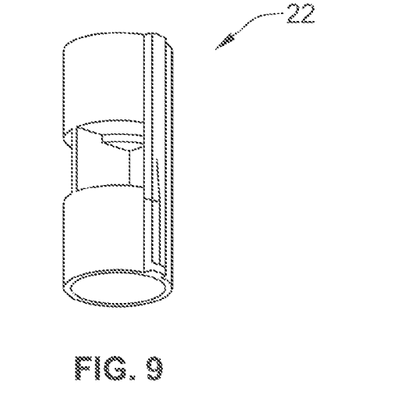
FIG. 9 is a perspective view of the reservoir of the medicated module of FIG. 2.
Figure 10:
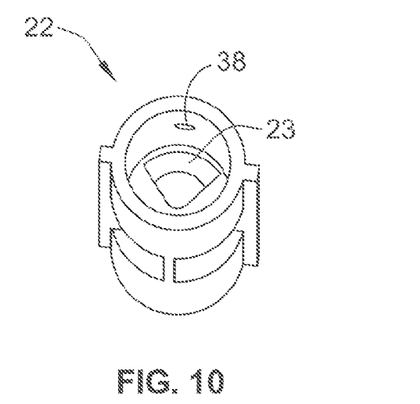
FIG. 10 is another perspective view of the reservoir of the medicated module of FIG. 2.

To minimize diffusion of the secondary medicament 2 contained in the capsule 31 within the medicated module 4 into the primary medicament during dispense of the medicaments, the reservoir 22 has an integral flow distributor 23. This flow distributor 23 helps to efficiently expel the secondary medicament 2 from the system and greatly minimizes residual volume. One possible embodiment of the reservoir 22 and flow distributor 23 is illustrated in FIGS. 9 and 10. Preferably, the reservoir 22 and the flow distributor 23 are manufactured as a single part from materials that are compatible with the secondary medicament 2, most preferably as a single molded piece. A preferred material would be that typically used to manufacture septa or pistons (bungs) found in multi-dose medicament cartridges, although any material that is compatible with the medicament during long-term storage would be equally applicable. The flow distributor 23 is configured and positioned in reservoir 22 such that the secondary medicament 2 fills flow channels that are defined by the shape and location of one or more channels (not shown) inside the reservoir 22. The shape of the flow channels can be optimized for a plug flow of medicament by varying the dimensions of the flow distributor 23 and/or channels. The cross-sectional area of the annulus formed between the flow distributor 23 and the wall of the reservoir 22 should be kept relatively small. The volume available to store the secondary medicament 2 would equal the internal volume of the reservoir 22 minus the volume of the flow distributor 23. Therefore, if the volume of the flow distributor 23 is marginally smaller than the internal volume of the capsule 31, a small volume is left which the secondary medicament 2 occupies. Hence, the scale of both the capsule 31 and the flow distributor 23 can be large while storing a small volume of the secondary medicament 2. Resultantly, for small volumes of secondary medicament 2 (e.g. 50 micro liters), the reservoir 22 can be of an acceptable size for handling, transport, manufacture, filling and assembly.

Preferably, the medicated module 4 is provided by a drug manufacturer as a stand-alone and separate device that is sealed to preserve sterility. The sterile seal of the module 4 is preferably designed to be opened automatically, e.g. by cutting, tearing or peeling, when the medicated module 4 is advanced or attached to the drug delivery device 7 by the user. Features such as angled surfaces on the end of the injection device 7 or features inside the module 4 may assist this opening of the seal.

The medicated module 4 should be designed to operate in conjunction with a multiple use injection device, preferably a pen-type multi-dose injection device, similar to what is illustrated in FIG. 1. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose and, preferably, a multi-dose device. However, in some cases it may be beneficial to use a single dose, disposable device.

A typical injection device contains the cartridge or other reservoir of primary medication. This cartridge is typically cylindrical in shape and is usually manufactured in glass. The cartridge is sealed at one end with a rubber bung and at the other end by a rubber septum. The injection device is designed to deliver multiple injections. The delivery mechanism is typically powered by a manual action of the user. However, the injection mechanism may also be powered by other means such as a spring, compressed gas or electrical energy.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A medicated module attachable to a drug delivery device, comprising,
   a housing;
   a distal needle and a proximal needle, both arranged within the housing, wherein the proximal needle is fixed in a hub connected to a proximal end of the housing;
   a reservoir arranged within the housing and being biased axially in a distal direction by a capsule spring, the reservoir comprising a single dose of a medicament prior to attachment to the drug delivery device, where the capsule spring is positioned within the housing to create a void space between the hub and the reservoir to prevent the proximal needle from fluid communication with the medicament in the reservoir and to provide a biasing force that offsets an axial displacement of a septum or a keeper hermetically sealing the reservoir at its proximal end;
   a needle guard adapted and arranged to provide protection of the distal needle;
   a needle guard spring having a distal end and a proximal end, where the proximal end engages the housing to bias the needle guard in a distal position to provide the protection of the at least one needle cannula;
   a selector operably connected to the reservoir, the selector being configured to enable selection between different operating conditions of the module for enabling the reservoir to overcome the biasing effect of the capsule spring and to move proximally to come into fluid engagement with the distal and proximal needles.

2. The medicated module of claim 1, wherein the selector is operably connected to the needle guard.

3. The medicated module according to claim 1, wherein the selector comprises one or more tactile features adapted and arranged to be gripped by a user, the tactile features being configured to allow movement of the selector with respect to the housing into one or more predetermined positions.

4. The medicated module of claim 3, wherein the selector positions comprise,
   a first position, where the needle guard is prevented from moving axially with respect to the housing, and where the proximal needle is not in fluid communication with the reservoir; and
   a second position, where movement of the needle guard in an axial direction with respect to the housing is allowed and where fluid communication of the proximal needle with the reservoir is enabled.

5. The medicated module according to claim 4, wherein, when the needle guard is moved axially with respect to the housing when the selector is in the second position, the reservoir is moved in a proximal direction with respect to the housing to enable fluid engagement of the proximal needle with the reservoir.

\* \* \* \* \*